US00PP11608P

United States Patent [19]

Olesen et al.

[11] Patent Number: Plant 11,608

[45] Date of Patent: Oct. 31, 2000

[54] COMPACT FLORIBUNDA ROSE PLANT NAMED 'POULAGUN'

[75] Inventors: L. Pernille Olesen; Mogens N. Olesen, both of Fredensborg, Denmark

[73] Assignee: Poulsen Roser ApS, Fredensborg, Denmark

[21] Appl. No.: 09/173,862

[22] Filed: Oct. 16, 1998

[51] Int. Cl.[7] ..... A01H 5/00

[52] U.S. Cl. ..... Plt./145

[58] Field of Search ..... Plt./145, 144, 118, Plt./125

[56] References Cited

U.S. PATENT DOCUMENTS

P.P. 10,729 12/1998 Olesen et al. ..... Plt./144

*Primary Examiner*—Howard J. Locker

[57] ABSTRACT

A new floribunda rose plant which has abundant, fragrant, yellow flowers, becoming ivory-yellow with age, and attractive foliage. The variety successfully propagates from softwood cuttings and by traditional budding and is suitable for year round production in commercial glasshouses. This new and distinct variety has shown to be uniform and stable in the resulting generations from asexual propagation.

1 Drawing Sheet

SUMMARY OF THE INVENTION

The present invention constitutes a new and distinct variety of compact floribunda rose plant which originated from a controlled crossing between Mini-Poul and an unnamed seedling. The two parents were crossed and the resulting seeds were planted in a controlled environment. The new variety is named 'POULagun'.

The new rose may be distinguished from its seed parent, Mini-Poul, by the following combinatioin of characteristics:

1. Mini-Poul is a yellow-red bicolor miniature rose and 'POULagun' is a compact floribunda rose with yellow, becoming ivory yellow with age flowers.

2. The flowers and growth of Mini-Poul are smaller than 'POULagun'.

3. The foliage of Mini-Poul is smaller than 'POULagun'.

The new variety may be distinguished from its pollen parent, an unnamed seedling created by the same inventors, by the following combination of characteristics:

1. The unnamed seedling is a yellow miniature rose and 'POULagun' is a compact floribunda rose with yellow, becoming ivory yellow with age flowers.

2. The flowers and growth of the unnamed seedling are smaller than 'POULagun'.

3. The unnamed seedling is an offspring of RUImired, U.S. Plant Pat. No. 5,770 and a yellow patio rose.

The objective of the hybridization of this rose variety for commercial greenhouse culture was to create a new and distinct variety with unique qualities, such as:

1. Uniform and abundant flowers;

2. Vigorous and compact growth;

3. Year-round flowering under glasshouse conditions;

4. Suitability for production from softwood cuttings in pots;

5. Durable flowers and foliage which make a variety suitable for distribution in the floral industry.

This combination of qualities is not present in previously available commercial cultivars of this type and distinguish 'POULagun' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULagun' was selected by the inventors as a single plant from the progeny of the hybridization in March, 1992.

Asexual reproduction of 'POULagun' by cuttings was first done by L. Pernille and Mogens N. Olesen in their nursery in Fredensborg, Denmark in May, 1993. This initial and other subsequent propagations conducted in controlled environments have demonstrated that the characteristics of 'POULagun' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULagun'. Specifically illustrated in SHEET 1:

1. Stem showing branching and the attachment of leaves, buds, and peduncles;

2. Flower bud, partially opened bud, and open bloom;

3. Flower petals, detached;

4. Sepals, receptable, and pedicel;

5. Flowering stem as well as a bare stem;

6. Leaves.

DETAILED DESCRIPTION OF THE VARIETY

The following is a description of 'POULagun', as observed in its growth in glasshouses in Fredensborg, Denmark, and in a field nursery in Jackson County, Oreg. Color references are made using The Royal Horticultural Society (London, England) Colour Chart, 1995, except where common terms of color are used.

For a comparison, several physical characteristics of the rose variety 'POULgret', a white floribunda rose variety from the same inventors described and illustrated in U.S. Plant Pat. No. 10,729 are compared to 'POULagun' in Chart 1.

CHART 1

| | 'POULagun' | 'POULgret' |
|---|---|---|
| Color, upper side of petal | Yellow-Orange Group 18B | White Group 155B |
| Color, reverse side of petal | Yellow-Orange Group 18C | White Group 155B |
| Thorns | None | Average |

Parents: Mini-Poul×unnamed seedling.
Classification:
*Botanical.*—*Rosa hybrida.*
*Commercial.*—Compact Floribunda.

FLOWER AND FLOWER BUD

Blooming habit: Continuous.
Flower bud:
*Size.*—Upon opening, 20 mm–25 mm in length from base of receptacle to end of bud.
*Bud form.*—Globular to pointed ovoid.
*Bud color.*—As sepals unfold, Yellow Group 8D. Yellow Group 8D at ¼ opening with intonations of Orange Group 29C and Orange-Red Group 34C.
*Sepals.*—Green Group 137D. Moderate foliaceous appendages on three of the five sepals. Surfaces of sepals slightly pubescent. Stipitate glands present on margins and outermost surfaces of sepals with appendages.
*Receptacle.*—Surface: Smooth. Occasionally glaucous. Shape: Urn-shaped. Size: Medium. 7–8 mm (h)×7–8 mm (w). Color: Green Group 143B with intonations of Greyed-Red Group 179A.
*Peduncle.*—Surface: Smooth. With moderate numbers of stipitate glands. Length: 30–40 mm average length. Color: Green Group 143B. On plants grown under high light conditions, penduncles may exhibit intonations of Greyed-Red Group 184A. Strength: Upright.
*Borne.*—In small clusters.
Flower bloom:
*Fragrance.*—Moderate floral to resinous fragrance.
*Duration.*—As a pot plant, flowers last from 8 to 10 days. As a cut flower 6 to 8 days. On a plant in the garden, the blooms have a duration on the plant of approximately 7 to 12 days. Petals fall cleanly away from plant.
*Size.*—Average flower diameter is 60–70 mm when open.
*Form.*—Shape of flower when viewed from the side: Upon opening, upper part: Flattened convex. Upon opening, lower part: Flattened Convex. Open flower, upper part: Flat. Open flower, lower part: Flat to concave.
*Petalage.*—Double. Average range: 30–35 under normal conditions with no petaloids.
Color:
*Upon opening, petals.*—Outermost petals: Upper Surface: Yellow-Orange Group 18B. Reverse Side: Yellow-Orange Group 18C. Innermost petals: Upper Surface: Yellow-Orange Group 18C. Reverse Side: Yellow-Orange Group 18C.
*Upon opening, basal petal spots.*—Petals: Outer Side: Yellow Group 9B. Inner Side: Yellow Group 9C.
*After opening, petals.*—Outermost petals: Upper Surface: Yellow-Orange Group 18C. Reverse Side: Yellow-Orange Group 18D. Innermost petals: Upper Surfaces: Yellow-Orange Group 18C. Reverse Side: Yellow-Orange Group 18D.
*Upon opening, basal petal spots.*—Petals: Outer Side: Yellow Group 9C. Inner Side: Yellow Group 9D.
General tonality: On open flower Yellow-White Group 158B. No change in the general tonality at the end of the third day. Afterwards, general tonality is Yellow-White Group 158C.
Petals:
*Petal reflex.*—Petals reflex slightly.
*Petal edge.*—With point in center of margin. Ruffled.
*Shape.*—Round to broadly deltoid.
*Petaloids.*—Commonly none.
*Thickness.*—Thick.
*Arrangement.*—Informal.
Reproductive organs:
*Pollen.*—Color: Yellow-Orange Group 16B. Abundance: Average.
*Anthers.*—Size: Medium. Color: Yellow-Orange Group 16B. Abundance: Average.
*Filaments.*—Color: Green-Yellow Group 1B.
*Stigmas.*—Stigmas superior in location to anthers. Color: Green-White Group 157C with intonations of Red-Purple Group 57C.
*Styles.*—Color: Green-White Group 157C with intonations of Red-Purple Group 57C.
*Hips.*—None observed.

PLANT

Plant growth: Vigorous and upright to bushy. When grown as a 15 cm pot plant, the average height of the plant itself is 24 to 28 cm and the average width is 22 to 24 cm. When grown as a nursery plant on its own roots, the average height of the plant itself is 55–65 cm and the average width is 35–45 cm.
Stems:
*Color.*—Young wood: Yellow-Green Group 146C. Older wood: Yellow-Green Group 146C.
*Prickles.*—Incidence: Thornless.
*Surface.*—Young wood: Smooth. Older wood: Smooth.
Plant foliage: Normal number of leaflets on normal leaves in middle of the stem: 5–7 leaflets.
*Leaf size.*—Medium. 60 mm×65 mm (w) average.
*Abundance.*—Above average abundance.
*Color.*—Upper Leaf Surface: Green Group 137A–Yellow-Green Group 147A. Lower Leaf Surface: Green Group 138B. Juvenile foliage: Green Group 137C. Anthocyanin intonation: Limited. Location: Leaf petiole, rachis, and leaflet margin. Color: Greyed-Red Group 179B.
Plant leaves and leaflets:
*Stipules.*—Present. Limited number of stipitate glands present on margins. Size: 12 mm–15 mm. Color: Green Group 137D.
*Petiole.*—Length: 20 mm – 25 mm. Color: Green Group 137C. Underneath: Smooth. Margins: With limited numbers of stipitate glands.
*Rachis.*—Color: Green Group 137C. Underneath: Smooth. Margins: With limited numbers of stipitate glands.
*Leaflet.*—Edge: Serrated. Shape: Ovate to round.
*Other.*—Moderately glossy finish. Leathery texture.
Disease resistance: Average resistance to black spot and Botrytis under outdoor growing conditions in Jackson County, Oreg.

We claim:

1. A new and distinct variety of rose plant of the compact floribunda class, substantially as herein illustrated and described as a distinct and novel rose variety due to its abundant and fragrant flowers, vigorous and compact growth, year round flowering under glasshouse conditions, suitability for production from softwood cuttings and traditional budding, and durable flowers and foliage which make the variety suitable for distribution in the floral industry.

* * * * *

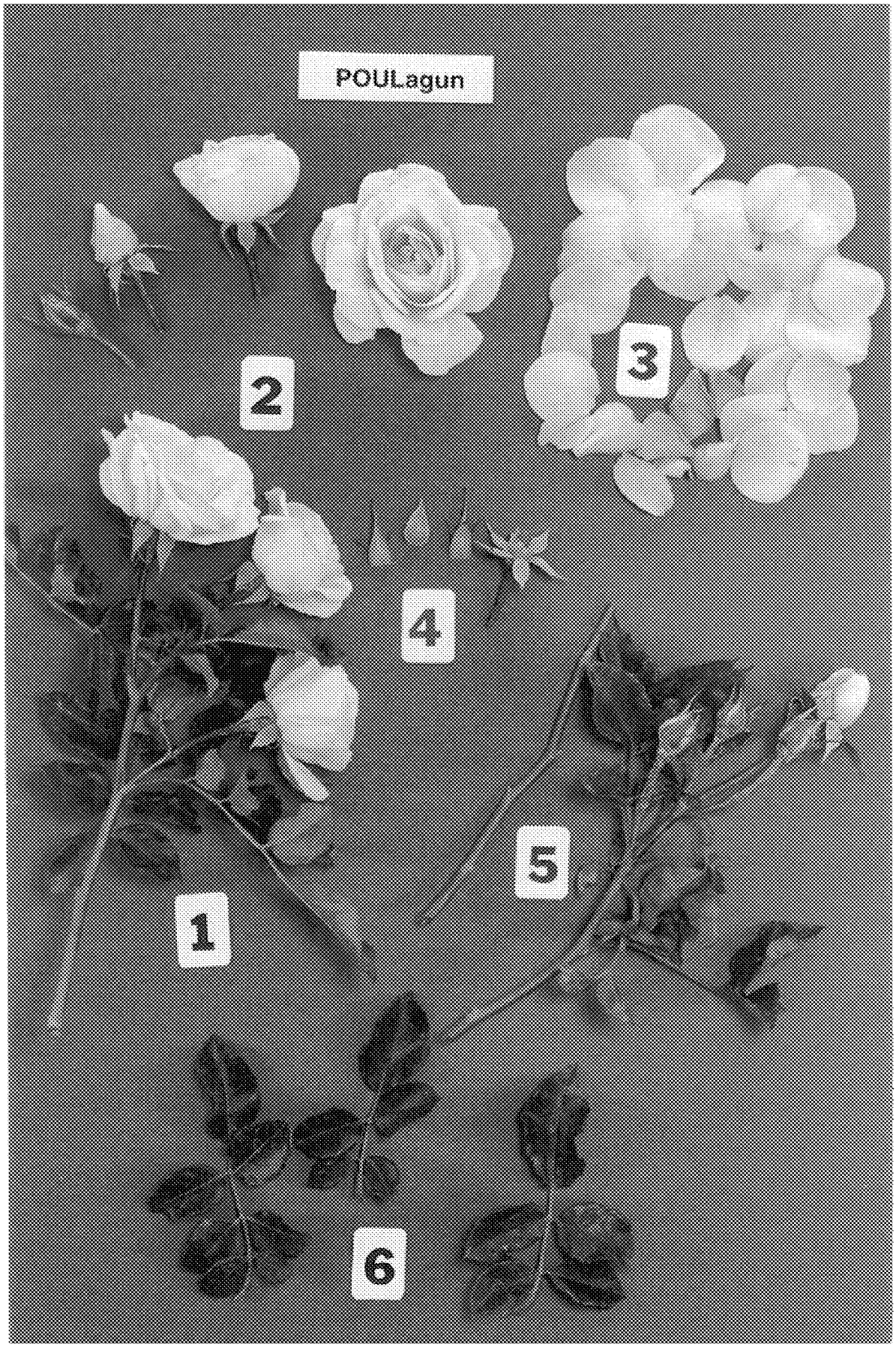
POULagun
2
3
4
5
1
6